United States Patent [19]
Morikawa

[11] Patent Number: 5,244,631
[45] Date of Patent: Sep. 14, 1993

[54] TESTING DEVICE

[75] Inventor: Naoki Morikawa, Nakakoma, Japan

[73] Assignee: Terumo Kabushiki Kaisha, Tokyo, Japan

[21] Appl. No.: 761,495

[22] Filed: Sep. 18, 1991

[30] Foreign Application Priority Data

Sep. 19, 1990 [JP] Japan .................................. 2-249867

[51] Int. Cl.$^5$ ........................................... G01N 31/22
[52] U.S. Cl. ..................................... 422/56; 422/57; 422/58; 436/66; 436/169
[58] Field of Search ................................ 422/56–58; 436/66, 169, 170

[56] References Cited

U.S. PATENT DOCUMENTS

| 4,578,358 | 3/1986 | Oksman et al. | 436/66 |
| 4,673,654 | 6/1987 | Talmage | 436/66 |
| 5,071,623 | 12/1991 | Akutsu | 436/66 X |

Primary Examiner—Jill A. Johnston
Attorney, Agent, or Firm—Burns, Doane, Swecker & Mathis

[57] ABSTRACT

A testing device includes a platelike stick and a detecting function part deposited on said stick. The stick is composed of a water-disintegrable layer, a water-soluble layer superposed on at least one surface of the water-disintegrable layer in the part thereof destined to contact an analyte fluid, and a multiplicity of minute pieces of a water-soluble material superposed on the opposite surfaces of the stick at least in the part thereof destined to contact with analyte fluid.

19 Claims, 1 Drawing Sheet

TESTING DEVICE

BACKGROUND OF THE INVENTION

1. Field of the Invention

This invention relates to a testing device to be used in testing body liquids such as urine, blood, abdominal dropsy, spinal fluid, and saliva and other liquids (such as drinking water and waste water).

2. Description of the Prior Art

Heretofore, as a testing device for detecting components of a body liquid (humor) such as urine, a ribbon-like stick (supporting member) having a detecting function part capable of inducing a color-yielding reaction with the component of interest deposited on one surface of the stick has been known to the art.

In the conventional testing device, a substance such as resin of polystyrene which possesses suitable rigidity and waterproofness has been utilized for the material of the stick thereof.

This testing device, once used, cannot be discarded hygienically because it is smeared with the sample liquid. When the used testing device is discarded as it is, it has the possibility of nursing a pathogenic microorganism and consequently causing propagation of an infectious disease. It has been customary, therefore, to discard the used testing device as contained in a pouch of synthetic resin or dispose of it by incineration.

The disposal of the used testing device is extremely irksome as described above. Thus, the desirability of developing a testing device which can be easily disposed after use has been finding growing recognition.

For the purpose of solving the problem mentioned above, a testing device which has a detecting function part deposited on a stick and has this stick formed of a water-disintegrable material such as polyvinyl alcohol or polyvinyl pyrrolidone (JP-A-62-24,145) and a testing device which has a detecting part deposited on a stick and has this stick formed of a water-soluble stick proper such as a water-soluble paper excellent in disintegrability in water and a coating formed on the stick proper and made of a water-soluble substance such as polyvinyl alcohol or polyethylene oxide incapable of being substantially dissolved until the observation of the reaction caused on the detecting function part is completed (JP-A-1-121,752) have been proposed.

In the former testing device, though the stick thereof is made of such a water-soluble material as polyvinyl alcohol, it is dissolved slowly and it retains a viscous state until it is dissolved completely. If this testing device after use is disposed of by being thrown into a flush toilet, for example, the stick thereof adheres so fast to the inner wall of the toilet bowl as to defy the force of the flushing water and eventually defiles the toilet bowl.

The latter testing device has been proposed for the purpose of overcoming the problem of the former testing device. The latter testing device, owing to its unduly high dissolving speed, has the possibility of being deformed in the shape of a roll between the time the stick is brought into contact with a body liquid under test and the time the reaction of the components of the body liquid with the detecting function part is observed and determined. There are times when the stick fails to discharge fully its inherent role of supporting the detecting function part. Particularly when this testing device is deformed as described above, it becomes difficult for the testing device to be set properly in a measuring instrument and used for rating the results of the test.

An object of this invention, therefore, is to provide a novel testing device.

Another object of this invention is to eliminate the drawbacks of the conventional techniques described above and, to this end, provide a testing device which retains prescribed rigidity intact until the test is completed and undergoes immediate dissolution and dispersion on contact with water.

SUMMARY OF THE INVENTION

The objects described above are accomplished by a testing device which comprises a platelike stick and a detecting function part deposited on the stick, the stick being composed of a water-disintegrable layer, a water-soluble layer superposed on at least one of the opposite surfaces of the water-disintegrable layer at least on the part thereof destined to contact an analyte fluid, and a multiplicity of minute pieces of a water-soluble material superposed on the opposite surfaces of the stick at least in the part thereof destined to contact with the analyte fluid.

This invention also discloses a testing device wherein the water-soluble layer is made of a water-soluble material which dissolves more slowly than the water-disintegrable layer. This invention further discloses a testing device wherein the stick is capable of retaining the detecting function intact even after contact thereof with an analyte fluid. This invention discloses a testing device wherein the minute pieces are regularly arranged on the surfaces of the stick. This invention also discloses a testing device wherein the minute pieces are square in shape. This invention further discloses a testing device wherein the minute pieces have a thickness in the range of from 1 to 15 $\mu$m. This invention discloses a testing device wherein the minute pieces each have a surface area in the range of from 0.01 to 64 mm$^2$. This invention also discloses a testing device wherein the total surface area of the minute pieces accounts for a proportion in the range of from 30 to 80%, based on the gross total surface area of the part of the stick destined to contact with an analyte fluid.

The testing device of the present invention retains prescribed rigidity intact between the time it is brought into contact with an analyte fluid and the time the test is completed and undergoes immediate dissolution and dispersion on contact with water. Thus, the testing device is easy to dispose. When it is dissolved in water, the resultant solution exhibits highly satisfactory flowability. This testing device, therefore, has no possibility of clogging the sewage pipes.

EXPLANATION OF THE PREFERRED EMBODIMENT

Now, one embodiment of the present invention will be described below with reference to the accompanying drawings.

Figure 1:
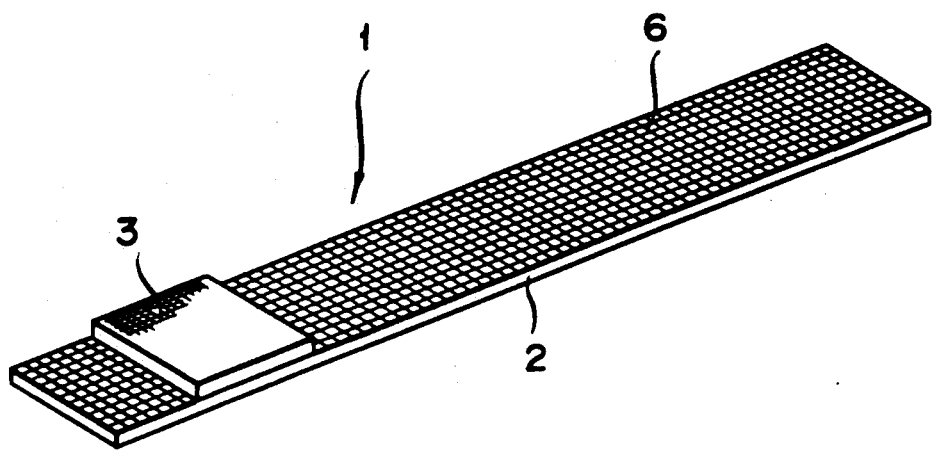
FIG. 1 is a perspective view of a testing device according with the present invention.

FIG. 1 is an overall perspective view illustrating one embodiment of the present invention. A testing device 1 illustrated in FIG. 1 comprises a platelike stick 2 and a detecting function part 3 attached to at least one surface of the stick 2. The detecting function part 3 is produced by impregnating a porous carrier with a reagent used for the purpose of testing. The kind of reagent is variable with the components to be detected in a given analyte fluid. The reagents which are usable effectively for the detection of proteins include a pH indicator such as tetrabrom phenol and the like (protein error method). The reagents which are usable for the detection of nitrites include diazotizing agents such as arsanilic acid and sulfanilamide and coupling agents such as N-(1-naphthyl)-ethylene diamine dihydrochloride and N,N-dimethyl naphthylamine, for example. The reagents which are usable for the detection of bilirubin include diazo compounds such as p-aminobenzenesulfonic acid, 2,6-dichlorobenzene diazonium tetrafluoroborate, and 2-trifluoromethylbenzene diazonium, for example. The reagents which are usable for the detection of glucose include oxidases such as glucose oxidase and peroxidase and indicators such as ortho-tolidine, for example. The reagents which are usable for the detection of occult blood include peroxides such as 2,5-dimethylhexane-2,5-dihydroperoxide, and indicators such as ortho-tolidine, for example.

The carriers which are effectively usable for impregnation with such reagents for testing as mentioned above include papers such as filter paper, non-woven fabrics of glass fibers and plastic materials, porous plastics, and absorbent resins, for example. The carriers should preferably be adapted to avoid reacting with or dissolving in the reagents used for the impregnation and should preferably possess absorbency. Among other carriers cited above, filter paper proves to be particularly preferably.

The detecting function part completed by drying the reagent which has impregnated the carrier may need protection against possible deterioration by moisture or ambient gas during storage or service of the testing device. For the purpose of precluding this deterioration and protecting the detecting function part, the detecting function part or the testing device may be coated with a thin release film of polyethylene, polyvinyl chloride, polyvinylidene chloride, or nylon, for example. This protective thin film is removed immediately before the testing device is put to use.

The sample liquids on which the testing device can be effectively used include body liquid such as urine, blood, abdominal dropsy, spinal fluid, and saliva and other liquids such as drinking water and waster water.

Figure 2:
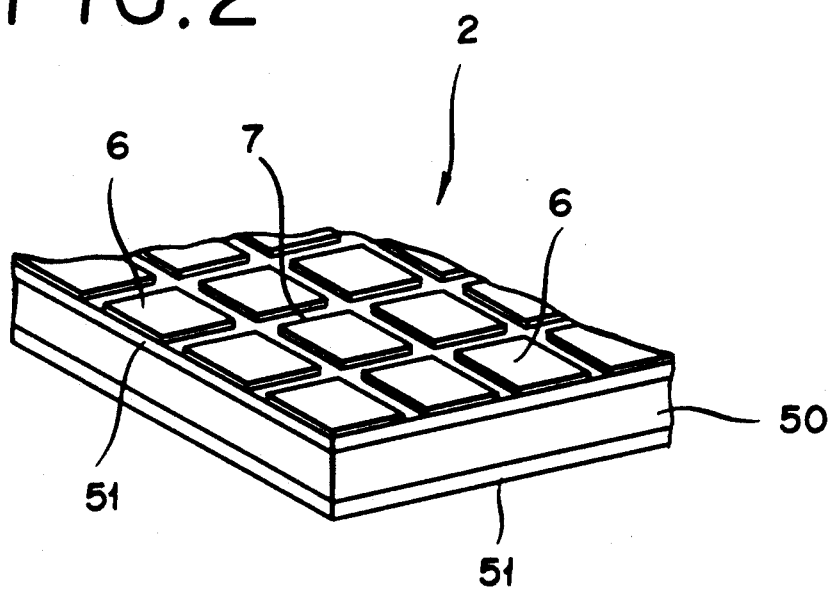
FIG. 2 is a partially magnified perspective view of a stick in the testing device of FIG. 1.

Now, the construction of the stick 2 will be described. The stick 2 is formed in the shape of a plate as illustrated in the drawing. The stick 2, as illustrated in FIG. 2, is possessed of several layers to be specifically described hereinabelow. Minute pieces 6 are deposited in a prescribed density on the opposite surfaces of the stick 2.

The stick 2 is provided with a water-disintegrable layer 50 and water-soluble layers 51 superposed one each on either or both of the opposite surfaces of the water-disintegrable layer 50. The water-disintegrable layer 50 is made of a water-disintegrable material which disintegrates on contact with water and entails dispersion of an insoluble constituent in the water. The water-disintegrable materials which are effectively usable herein include those produced by solidifying such water-insoluble materials as pulp, cellulose, synthetic fibers, and glass fibers in the form of sheet with such water-soluble materials as carboxymethyl cellulose sodium (CMC-Na), methyl cellulose, and polyacryl amide, for example.

In the stick 2 of the present embodiment, water-soluble paper is used as the water-disintegrable layer 50. To be specific, the product of Mishima Seishi K. K. marketed under the trademark designation of "Dissolvo" is used therefor. The thickness of the stick 2 is in the range of from 0.1 to 3 mm, preferably from 0.2 to 0.6 mm. If the thickness is less than 0.1 mm, rigidity becomes insufficient, and if it is more than 3 mm, solubility decreases and it invites increased cost.

The materials which are usable for the formation of the water-soluble layer 51 include polyvinyl alcohol (average polymerization degree 250 to 2,400), polyethylene oxide (average molecular weight 200 to 10,000) and polyvinyl pyrrolidone (molecular weight 10,000 to 360,000), for example.

The water-soluble layer 51 possesses rigidity of a certain level and retains this rigidity intact between the time the stick 2 is brought into contact with urine and the time the color assumed by the detecting function part 3 is rated. When the water-disintegrable layer 50 is brought into contact with such a sample fluid as urine, for example, the water-disintegrable material contained therein begins to disintegrate. The water-soluble material dissolves after the disintegration of the water-disintegrable material. The shape of the stick 2, therefore, remains intact until the water-soluble material is dissolved to a certain extent. After the testing device 1 has contacted the sample fluid, the sample fluid adheres to the periphery of the detecting function part 3. The testing device 1, therefore, is only required to possess a thickness such as to retain rigidity enough to defy dissolution or deformation otherwise causable with the amount of the sample fluid so adhering. The thickness of the water-soluble layer 51, therefore, is generally in the range of from 10 to 100 $\mu$m, preferably from 20 to 60 $\mu$m. The water-soluble layer 51 is not required to be superposed on the entire surface of the stick 2 but may be superposed on at least the part of the stick 2 destined to be immersed in the sample fluid.

The testing device 1 which has been used for the test is discarded in water. The time required for the testing device 1 so discarded in water after the test to be dissolved and completely dispersed therein can be adjusted by the ratio of the thickness of the water-disintegrating layer 50 to that of the water-soluble layer 51. In one example of the testing device 1 of the present embodiment, the water-disintegrable layer 50 have a thickness of 220 $\mu$m and the water-soluble layer 51 a thickness of 30 $\mu$m. Optionally, the testing device 1 is provided with one water-disintegrable layer 50 and one water-soluble layer 51.

The minute pieces 6 attached fast to the obverse and reverse surfaces of the stick 2 have a square or rectangular shape as illustrated in FIG. 2 and are arranged longitudinally and laterally as spaced by a fixed distance. The minute pieces 6 may be made of a water-soluble material. The materials which are usable for the minute pieces 6 include acrylic resin, vinyl chloride resin, polyesters, and polyurethane, for example. For the sake of good appearance, these minute pieces 6 may be colored by incorporation of a pigment.

In the part covered by the minute pieces 6, contact between the water-soluble layer 51 and water or a sample fluid is inhibited by the minute pieces 6. The time required for the stick 2 to be dissolved into water, therefore, can be adjusted also by the ratio of the total surface area of the minute pieces 6 to the gross total surface are of the stick 2. The part covered by the minute pieces 6 need not occupy the entire surface of the stick 2 but may occupy at least the part thereof destined to contact the sample fluid.

The minute pieces 6 are attached as by screen printing or gravure printing, for example, on the obverse and reverse surfaces of the stick 2. The thickness of the minute pieces 6 is approximately in the range of from 1 to 15 $\mu$m. Within this range, the thickness is desired to be as small as possible. The thickness of the minute pieces 6 may be approximately in the range of from 5 to 15 $\mu$m when they are deposited by screen printing or approximately in the range of from 1 to 10 $\mu$m when they are deposited by gravure printing. In the testing device 1 of the present embodiment, this thickness is about 5 $\mu$m. The length of the side of the minute square pieces 6 is in the range of from 0.1 to 8 mm, preferably from 0.2 to 3 mm. The surface area of each of the minute pieces is in the range of from 0.01 to 64 mm$^2$, preferably from 0.04 to 9 mm$^2$.

As already described, the time during which the stick 2 after contacting sample fluid continues to retain prescribed rigidity and discharge the inherent function of supporting and the time during which the testing device discarded in water is completely dissolved and dispersed can be adjusted by the aforementioned ratio in thickness between the water-disintegrable layer 50 and the water-soluble layer 51 and the ratio of the total surface area of the minute pieces 6 to the gross total surface area of the stick 2.

Incidentally, the testing device 1 by nature preferably possesses rigidity such that this device 1 after contacting a sample fluid remains intact until the color generated by the reaction is observed and determined completely and, at the same time, possess solubility such that the device 1 is quickly dissolved and dispersed when it is discarded in water. For this purpose of producing the testing device possessing this quality, it suffices to select the ratio of the water-soluble layer 51 to the water-disintegrable layer 50 approximately in the range of from 1 to 40% and the ratio of the total surface area of the minute pieces 6 to the gross total surface area of the stick 2 approximately in the range of from 30 to 80%. Preferably, the former ratio is in the range of from 5 to 25% and the latter ratio in the range of from 40 to 60%. These numerical values, however, are variable with the materials used for the water-disintegrable layer 50 and the water-soluble layer 51.

The minute pieces 6 need not be formed invariably in the shape of a square but may be formed in a circular shape or some other shape when desired.

Now, the operation of the testing device 1 constructed as described above will be explained. Urine as a sample fluid is brought into contact with the detecting function part 3 of the testing device 1. The detecting function part 3, on contact with the sample fluid, reacts therewith and indicates the presence/absence and concentration of the component of interest. At this time, the stick 2 has the contact surface thereof with the sample fluid limited by the minute pieces 6. Where the detecting function part 3 is expected to allow determination of the intensity of the reaction to be caused thereby with the sample fluid, the sample fluid is merely required to adhere to the periphery of the detecting function part 3. The possible deformation or dissolution of the stick 2, therefore, can be fully repressed by the minute pieces 6.

While the aforementioned determination by the detecting function part 3 is in process, specifically for a period of about five minutes, the stick 2 continues to possess rigidity enough to avoid being bent under its own weight.

When the testing device 1 is discarded in the bowl of a flush toilet, for example, after the determination performed by the detecting function part 3 is finished, the water infiltrates through gaps 7 between the minute pieces 6 and the edges of the platelike stick 2, immediately starts dissolving the water-disintegrable layer 50 and the water-soluble layer 51, and completer their dissolution in a matter of about two minutes. Since the minute pieces 6 are regularly arranged as spaced by a fixed distance, the stick 2 as a whole is uniformly dissolved. Though the water-soluble layer 51 grows viscous during the dissolution, it avoids sticking to the inner wall of the flush toilet because the surface thereof is covered with the minute pieces 6. The minute pieces 6 are scattered in the water after the stick 2 has been completely dissolved. Since they are individually small, they are readily washed away by the flush.

Now, the present invention will be described more specifically below with reference to working examples.

EXAMPLE 1

Water-soluble layers 51 having a thickness of 30 $\mu$m and made of polyvinyl alcohol (average polymerization degree about 1,500) are superposed one each on the opposite surfaces of a water-disintegrable layer 50 made of a water-soluble paper measuring 220 $\mu$m in thickness, 82 mm in length, and 5 mm in width (produced by Mishima Seishi K. K. and marketed under trademark designation of "Dissolvo"). On the surface of one of these water-soluble layers 51, minute pieces of acryl resin having a surface area of the square of 0.8 mm (0.64 mm$^2$) were deposited by gravure printing in a total quantity accounting for a proportion of 60% of the total surface area of the stick 2. The thickness of the minute pieces 6 was 5 $\mu$m.

A testing device was completed by causing a detecting function part 3 produced in advance by impregnating a filter paper (Toppan Shoji paper No. 5250) with a solution of a reagent for the detection of protein (tetrabrom phenol blue (buffer solution of pH 2.8)) and drying the wet filter paper to adhere fast through the medium of a both side adhesive tape (No. 5450, a product of Sugawara Kogyo K. K.) to the neighborhood of the leading terminal part of the stick 2 obtained as described above.

Control 1

A testing device was produced by applying fast the same detecting function part as used in Example 1 to a stick measuring 30 $\mu$m in thickness, 82 mm in length, and 5 mm in width and made of polyvinyl alcohol (average polymerization degree 3,000).

Control 2

A testing device was produced by following the procedure of Example 1, except that the superposition of the minute pieces was omitted.

EXAMPLE 2

The testing devices of Example 1 and Controls 1 and 2 were kept immersed in the urine from a patient for 1 second. The detecting function parts of the testing devices were visually examined to confirm detection of protein. Thereafter, the 50 testing devices were discarded one by one in the bowl of a flush toilet at a front part (that is, opposite part to an outlet) to find adhered testing devices to the bowl. The results were as shown in Table 1.

TABLE

| Sample | Results |
|---|---|
| Example 1 | 0/50 |
| Control 1 | 7/50 |
| Control 2 | 5/50 |

*Numeral 50 as a denominator means total discarded testing device and numerals as a numerator means number of adhered testing devices to the bowl.

What is claimed is:

1. A testing device comprising a platelike stick having opposite surfaces and a detecting function part deposited on at least one of said surfaces of said stick, said stick being composed of a water-disintegrable layer and a water-soluble layer superposed on at least one surface of said water-disintegrable layer in the part thereof destined to contact an analyte fluid, and including a multiplicity of minute pieces of water-insoluble material superposed on the opposite surfaces of said stick at least in the part thereof destined to contact with an analyte fluid.

2. A testing device according to claim 1, wherein said water-soluble layer is made of a water-soluble material which dissolves more slowly than said water-disintegrable layer.

3. A testing device according to claim 2, wherein said stick is capable of retaining the detecting function after contact with said analyte fluid.

4. A testing device according to claim 1, wherein said minute pieces have a square shape.

5. A testing device according to claim 1, wherein said minute pieces have a thickness in a range of from 1 to 15 $\mu$m.

6. A testing device according to claim 1, wherein said minute pieces each have a surface area in a range of from 0.01 to 64 mm$^2$.

7. A testing device according to claim 1, wherein the ratio of the total surface area of said minute pieces to the gross total surface of the part of said stick destined to contact said sample fluid is in the range of from 30% to 80%.

8. A testing device according to claim 1, wherein said water-disintegrable layer is produced by solidifying a water-insoluble fibrous material with a water-soluble binder.

9. A testing device according to claim 1, wherein said water-soluble layer and said minute pieces are superposed on the entire surface of said stick.

10. A testing device comprising a platelike stick having opposite surfaces and a detecting function part deposited on at least one of said surfaces of said stick, said stick being composed of a water-disintegrable layer and a water-soluble layer superposed on at least one surface of said water-disintegrable layer in the part thereof destined to contact an analyte fluid, and including a multiplicity of minute pieces of water-insoluble material superposed on the opposite surfaces of said stick at least in the part thereof destined to contact an analyte fluid, said minute pieces being regularly arranged on the surface of said stick and said minute pieces have a thickness in a range of from 1 to 15 $\mu$m.

11. A testing device according to claim 10, wherein said water-soluble layer is made of a water-soluble material which dissolves more slowly than said water-disintegrable layer.

12. A testing device according to claim 10, wherein said stick is capable of retaining the detecting function after contact with said analyte fluid.

13. A testing device according to claim 10, wherein the ratio of the total surface area of said minute pieces to the gross total surface of the part of said stick destined to contact said sample fluid is in the range of from 30% to 80%.

14. A testing device according to claim 10, wherein said water-soluble layer and said minute pieces are superposed on the entire surface of said stick.

15. A testing device comprising a platelike stick having opposite surfaces and a detecting function part deposited on at least one of said surfaces of said stick, said stick being composed of a water-disintegrable layer and a water-soluble layer superposed on at least one surface of said water-disintegrable layer in the part thereof destined to contact an analyte fluid, and including a multiplicity of minute pieces of water-insoluble material superposed on the opposite surfaces of said stick at least in the part thereof destined to contact analyte fluid, said minute pieces being regularly arranged on the surface of said stick and said minute pieces each having a surface area in a range of from 0.01 to 64 mm$^2$.

16. A testing device according to claim 15, wherein said water-soluble layer is made of a water-soluble material which dissolves more slowly than said water-disintegrable layer.

17. A testing device according to claim 15, wherein said stick is capable of retaining the detecting function after contact with said analyte fluid.

18. A testing device according to claim 15, wherein the ratio of the total surface area of said minute pieces to the gross total surface of the part of said stick destined to contact said sample fluid is in the range of from 30% to 80%.

19. A testing device according to claim 15, wherein said water-soluble layer and said minute pieces are superposed on the entire surface of said stick.

* * * * *

UNITED STATES PATENT AND TRADEMARK OFFICE
CERTIFICATE OF CORRECTION

PATENT NO. : 5,244,631
DATED : September 14, 1993
INVENTOR(S) : Noaki Morikawa It is certified that error appears in the above-identified patent and that said Letters Patent is hereby corrected as shown below:

In column 3, line 33, delete "preferably" and insert --preferable--.
In column 4, line 58, delete "water-soluble" and insert --water-insoluble--.
In column 6, line 12, delete "completer" and insert --complete--.

Signed and Sealed this

Twenty-sixth Day of April, 1994

Attest:

BRUCE LEHMAN

Attesting Officer    Commissioner of Patents and Trademarks